United States Patent
Dinis Carmo

(10) Patent No.: US 9,782,192 B2
(45) Date of Patent: Oct. 10, 2017

(54) SURGICAL SET OF INSTRUMENTS FOR PRECISION CUTTING

(76) Inventor: José Dinis Carmo, Porto (PT)

(*) Notice: Subject to any disclaimer, the term of this patent is extended or adjusted under 35 U.S.C. 154(b) by 0 days.

(21) Appl. No.: 13/817,425

(22) PCT Filed: Dec. 10, 2010

(86) PCT No.: PCT/IB2010/055721
§ 371 (c)(1),
(2), (4) Date: Feb. 15, 2013

(87) PCT Pub. No.: WO2012/023006
PCT Pub. Date: Feb. 23, 2012

(65) Prior Publication Data
US 2013/0144318 A1 Jun. 6, 2013

(30) Foreign Application Priority Data
Aug. 18, 2010 (PT) .......................................... 105255

(51) Int. Cl.
*A61B 17/32* (2006.01)
(52) U.S. Cl.
CPC ............... *A61B 17/320036* (2013.01); *A61B 17/320016* (2013.01); *A61B 2017/320052* (2013.01)
(58) Field of Classification Search
CPC .... A61B 17/320036; A61B 17/320016; A61B 2017/320052; A61B 17/1728;
(Continued)

(56) References Cited

U.S. PATENT DOCUMENTS

| 4,781,202 A | * | 11/1988 | Janese | A61B 10/0266 600/567 |
| 5,253,659 A | * | 10/1993 | McNamara | A61B 17/32001 128/898 |
| 5,297,340 A | * | 3/1994 | Kahlcke | 30/155 |
| 5,299,357 A | | 4/1994 | Wonderley et al. | |

(Continued)

FOREIGN PATENT DOCUMENTS

| WO | WO 93/22978 A1 | 11/1993 |
| WO | WO 94/26182 A1 | 11/1994 |

(Continued)

OTHER PUBLICATIONS

International Search Report, dated Jul. 25, 2011 in connection with PCT International Application No. PCT/IB2010/055721, filed Dec. 10, 2010.

(Continued)

*Primary Examiner* — Katherine M Shi
*Assistant Examiner* — Mohamed Gabr
(74) *Attorney, Agent, or Firm* — Lucas & Mercanti, LLP

(57) ABSTRACT

A method and set of instruments are disclosed particularly useful for carpal tunnel surgeries that allow a precision cut in the transverse carpal ligament (TCL) without direct vision or exposure of the ligament, except for its most proximal edge, but with guidance and safety of the cutting knife, eliminating or, at least very much decreasing, the probability of cutting lines in the wrong direction and inadvertent (iatrogenic) lesions to the surrounding structures. In one preferred embodiment the instrument comprises: a uniquely shaped cannulated guide rod, through which passes a flexible metal guide needle (33) which serves as a guideline for a uniquely shaped cutting knife or fasciotome (25) having a cannulated finger-like prong in the inferior edge of the blade portion of the knife.

17 Claims, 22 Drawing Sheets

(58) Field of Classification Search
 CPC . A61B 17/3421; A61B 17/0218; A61B 17/02;
           A61B 17/1714; A61B 17/3403; A61B
           17/3417; A61B 2017/0256; A61B
           2017/2904; A61M 25/09
 USPC .............. 606/108, 117, 137, 167, 170, 191;
           30/155; 128/898; 604/131; 600/104
 See application file for complete search history.

(56) References Cited

U.S. PATENT DOCUMENTS

| | | | | |
|---|---|---|---|---|
| 5,366,465 | A | * | 11/1994 | Mirza ................ A61B 17/3417 |
| | | | | 128/898 |
| 5,586,564 | A | * | 12/1996 | Barrett et al. ................ 128/898 |
| 5,620,446 | A | * | 4/1997 | McNamara ...... A61B 17/32003 |
| | | | | 128/898 |
| 5,957,944 | A | | 9/1999 | Khuri |
| 6,159,179 | A | * | 12/2000 | Simonson .......... A61B 17/0218 |
| | | | | 604/117 |
| 8,025,670 | B2 | | 9/2011 | Sharp et al. |
| 8,608,763 | B1 | * | 12/2013 | Jurbala ............ A61B 17/32003 |
| | | | | 606/170 |
| 2003/0187454 | A1 | * | 10/2003 | Gill ....................... A61F 2/4425 |
| | | | | 606/99 |
| 2004/0054378 | A1 | * | 3/2004 | Yang ................ A61B 17/32003 |
| | | | | 606/191 |
| 2006/0190021 | A1 | * | 8/2006 | Hausman et al. ............ 606/167 |
| 2007/0010840 | A1 | * | 1/2007 | Rosenthal .......... A61B 17/3207 |
| | | | | 606/170 |
| 2009/0048620 | A1 | | 2/2009 | Weiss et al. |
| 2009/0157002 | A1 | * | 6/2009 | Dumot ............... A61B 18/0218 |
| | | | | 604/131 |
| 2009/0216234 | A1 | * | 8/2009 | Farr ..................... A61B 17/025 |
| | | | | 606/79 |
| 2010/0069944 | A1 | * | 3/2010 | Murakami ....... A61B 17/00008 |
| | | | | 606/184 |
| 2011/0087258 | A1 | * | 4/2011 | Sluss ............................ 606/170 |

FOREIGN PATENT DOCUMENTS

| | | |
|---|---|---|
| WO | WO 03/045290 A1 | 6/2003 |
| WO | WO 2010/030872 A2 | 3/2010 |

OTHER PUBLICATIONS

Written Opinion of the International Searching Authority, dated Jul. 25, 2011 in connection with PCT International Application No. PCT/IB2010/055721, filed Dec. 10, 2010.

* cited by examiner

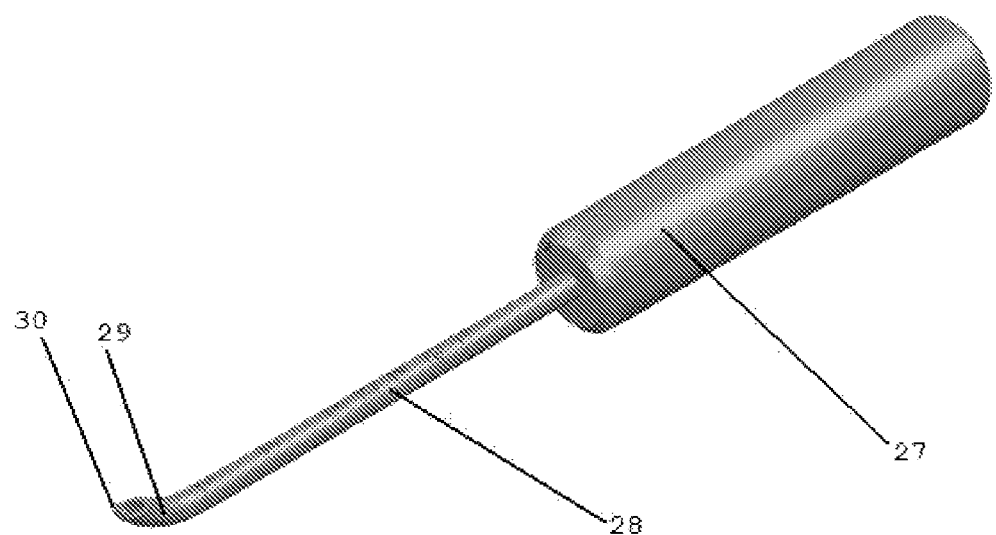
Figure 10
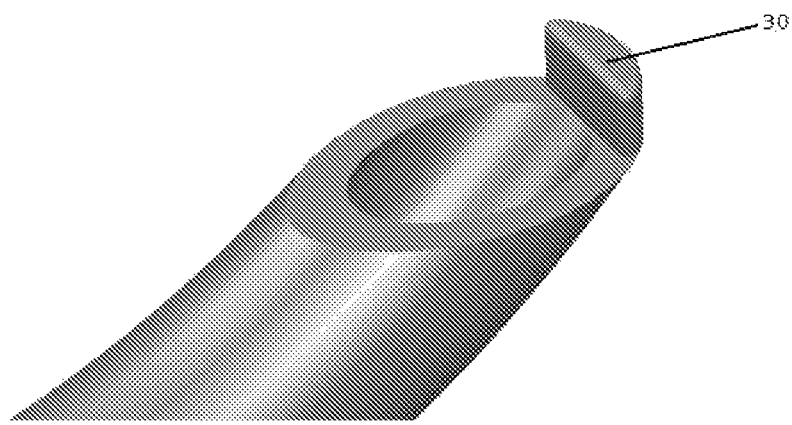
Figure 11-A

SURGICAL SET OF INSTRUMENTS FOR PRECISION CUTTING

CROSS-REFERENCE TO RELATED APPLICATIONS

This application is a §371 national stage of PCT International Application No. PCT/IB2010/055721, filed Dec. 10, 2010, claiming priority of Portuguese Patent Application No. 105255, filed Aug. 18, 2010, the contents of each of which are hereby incorporated by reference in its entirety.

FIELD OF THE INVENTION

This invention relates to a set of surgical instruments for precision cutting, particularly suited for carpal tunnel release surgeries. The method for performing the release is also disclosed.

The surgical set of instruments developed for use specially, but not exclusively, in carpal tunnel release surgery, comprises a cannulated guide rod, a cutting knife or fasciotome, a cutting knife or fasciotome with a curved shaft at 90° and a slotted guide cannula. The present invention comprises a method of performing a transverse carpal tunnel release that is designed to be carried out without the need to expose and/or to vision the entire ligament before cutting, albeit with fully controlled and cutting accuracy of the release, eliminating or, at least, very much decreasing, the probability of cutting lines in the wrong direction and inadvertent (iatrogenic) lesions to the surrounding structures.

BACKGROUND OF THE INVENTION

Description of the Prior Art

Carpal tunnel syndrome is a complex of symptoms resulting from compression of the median nerve in the carpal tunnel. Carpal tunnel is the osseo-fibrous passage for the median nerve and flexor tendons, formed by the flexor retinaculum and the carpal bones. Carpal bones are the bones of the carpus. Carpus or wrist is the region of the articulation between the forearm and the hand, which is made up of eight bones. Flexor retinaculum or transverse carpal ligament is a heavy fibrous band continuous with the distal part of the antebrachial fascia, completing the carpal tunnel.

Antebrachial fascia or (deep) fascia of the forearm is the investing fascia of the forearm. Fascia is a sheet or band of fibrous tissue such as lies deep to the skin or forms an investment for muscles (and various organs of the body).

The treatment of carpal tunnel syndrome by releasing the transverse carpal ligament has been utilized for over 60 years. During that time several methods for releasing the ligament have been developed.

In summary, they can be classified into two major groups: 1) open methods, using an incision in the skin of the volar aspect of the palm over the ligament and 2) endoscopic methods. Endoscopic methods can be further divided into two subgroups: 2) a) one using one single incision and 2) b) another using two incisions, being at least one in the patient's palm.

1) Open methods are all performed basically in the same way, with some variants, relating mainly to the length of the skin incision and/or its exact positioning in the palm. Although very effective in relieving most patients' symptoms and safe (the safety of the procedure generally varying inversely with the length of the scar) they can require relatively lengthy post-operative recuperation for the hand and not infrequently are complicated by tenderness around the incision site and the so called "pillar pain", pain at the base of the thenar and hypothenar eminences, just distal to the wrist crease and on each side of the surgical scar.

REFERENCES

U.S. Patent Documents

U.S. Pat. No. 5,387,222 02/1995 Strickland. Carpal Tunnel Tome and Carpal Tunnel Release Surgery U.S. Pat. No. 5,413,5802 05/1995 Stephenson. Carpal Tunnel Knife U.S. Pat. No. 5,908,433 06/1999 Eager. Carpal Tunnel Knife 2) In an attempt to minimize these complications several endoscopic methods for division of the transverse carpal ligament were developed, receiving considerable popularity especially during the 80 s and 90 s.

In general, these techniques employ the passage of a special instrument beneath the transverse carpal ligament, such as, for example, the method shown in U.S. Pat. No. 5,273,024 to Menon, and then utilize fiberoptics and special cutting devices to observe and divide the ligament. However these techniques are riddled with problems, including the need of special expensive equipment, requiring specialized training and long learning curves from the part of the surgeon, being a rather lengthy procedure. They have also been challenged as not always being consistent in their ability to divide completely the transverse carpal ligament and there are reports of complications such as iatrogenic injury to the contents of the carpal tunnel, namely the median nerve and its branches and tendons inside the carpal tunnel. In some cases the instrument was driven into the wrong passageway causing injury to the ulnar nerve and artery. Not infrequently, during the operation, the vision of the intended structures is significantly impaired by fogging of the tip of the lens of the optic instrument, or by palmar fat dropping into the working field as the transverse carpal ligament is being released. If the technique implies the use of a "small" palmar incision, the problem of local and pillar pain may be diminished but it is not entirely eliminated.

Besides all these reasons, it is the personal opinion of the inventor that one of the major drawbacks of the endoscopic techniques is the need for previous dilation of the content of the carpal tunnel, using a quit of "dilators" to make room for introducing the cutting apparatus. The fundamental reason why carpal tunnel syndrome develops in the first place is because both the structures that bound and fill the carpal vault are virtually incompressible, therefore, if the contents swell, the median nerve becomes compressed triggering the symptoms. "Dilating" the contents of the canal adds to the very same problem one is trying to solve, at least temporarily, and is potentially dangerous because the pressure may move structures over or to the front of the cutting instrument, seriously endangering them.

REFERENCES

U.S. Patent Documents

U.S. Pat. No. 5,273,024 12/1993 Menon. Method and Apparatus for Performing Endoscopic Surgery U.S. Pat. No. 5,334,214 08/1994 Putnam. Apparatus and Method for Dividing Transverse Carpal Ligament Therefore, what is needed is a simple, safe, effective, and inexpensive technique that requires only a single wrist incision, in order to avoid or minimize to the maximum both complications and operative burdens.

In summary, the advantages offered by the present invention over the prior art are the following:

In Relation to the 1) Open Methods:

1) Avoiding all together any incision in the palm of the hand, therefore, eliminating or greatly diminishing incision pain and "pillar pain"

2) Smaller incision over the distal wrist crease

3) Less post-operative pain

4) Better cosmetic result: said incision becomes rapidly (in a few months) for all practical aspects undetectable In Relation to the 2) Endoscopic Methods:

Much simpler technique, avoiding:

1) The need of special (very) expensive equipment: the technique implies the use of only 4 or 5 simple, inexpensive tools;

2) The need for specialized training and long learning curves from the part of the surgeon;

3) Fast procedure;

4) No need for the previous dilation of the content of the carpal tunnel;

4) Reliable and reproducible technique;

5) Able to ensure a complete release of the ligament in all cases;

5) Safe technique: in more than 100 cases performed by the inventor no cases of significant complications have been detected.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

The present invention relates to a set of surgical instruments particularly suited, but not exclusively, for carpal tunnel release surgeries, and its method of use, which allows the performance of an incision in the TCL without direct vision of the ligament, except for its most proximal border, but with guidance and safety when handling the knife, eliminating or greatly reducing the probability of cutting lines in the wrong direction. Said set comprises:

A cannulated guide rod (28), FIG. 10, with a curved distal extremity, guiding the passage of a flexible metal guide needle (33) across a selected point in the palm of the hand A cutting knife or fasciotome (25), FIG. 12, which comprises, at least, one cannulated finger-like prong (20 or 24) attached to the inferior surface of the blade holder (21) located in the head portion of the device, and one or two finger-like solid prongs (22; 23) extending forwardly above and below the blade, similar to the type of surgical knife found in U.S. Pat. No. 5,387,222 issued to Strickland.

Alternatively, the lower end of the blade portion may be flat or rounded at the end, extending below the blade, replacing the inferior solid finger-like prong (22). Attached to the bottom surface of said finger-like solid prong (22), or its replacement surface, there are one or two finger-like cannulated prongs (20 and 24). The purpose of said finger-like cannulated prongs is to allow the passage of the flexible metal guide needle (33), after this needle is placed under the under surface of the (TCL) (106), with the help of the curved cannulated guide rod (28). This needle will guide the progression of said blade (21) of said distal end of the fasciotome (25) during the cutting action, therefore, eliminating the possibility of the device deviating from the intended route into any wrong passageway. In the distal part of the fasciotome (25) shaft there is also a set of holes or fenestrations (26), placed at regular, referenced, distances from the tip of the instrument and to each other for the purpose of determining the length of device introduced into the palm and therefore the length of cut transverse carpal ligament (TCL). The fasciotome also includes a handle (34) attached to the proximal (rear) end of the shaft, in order to make it easier and safer to push the device along through the ligament, as shown in FIG. 15. At the end of the upper finger-like prong there is, in a preferred form of embodiment, a metal sphere (32), with the preferred size of 2 mm, placed preferably eccentrically in order not to decrease the width of the blade. This sphere increases the bluntness of the finger-like prong, virtually eliminating the possibility of the blade to deviate from the intended route, namely downwards, across the transverse carpal ligament (TCL), towards the median nerve and tendons. However, its preferred size does not interfere with forward advancement of the fasciotome.

A cutting knife or fasciotome with a 90° angled curved shaft (41), coupled to any type of handle that the surgeon may consider appropriate for its use, and a blade holder with a blade portion (21) bounded by two finger-like solid prongs (22; 23) at the tip, extending forwardly above and below the blade, similar to the type of surgical knife found in U.S. Pat. No. 5,387,222 issued to Strickland. Alternatively, the lower end of the blade may be flat or rounded at the end, extending below the blade for the same distance, replacing the inferior finger like prong (22). At the end of each finger-like prong there is, preferably, a metal sphere (32), with the preferred size of 2 mm, placed preferably eccentrically, in order not to decrease the width of the blade portion. Said spheres increase the bluntness of the finger-like prongs, virtually eliminating the possibility of the blade to deviate from the intended route, either superficially, which could result in an incomplete cut or no cut of the distal antebrachial fascia or downwards, across the transverse palmar ligament, towards the median nerve and tendons. However, its preferred size does not interfere with forward advancement of the fasciotome.

A slotted (guide) cannula (40), with a closed but fenestrated distal end, by means of a central hole (33A), and an open proximal end, the cannula provided with a longitudinal slot (39) extending from a point adjacent the cannulated distal end to a point adjacent the open proximal end. The cannula can have a C or D-shaped interior cross-section with the flat part of the C or D-shape lying along the rim of the longitudinal slot.

The slot guides the fasciotome and the fenestration in the distal end allows for the passage of the flexible guide needle that will lead the fasciotome across the transverse carpal ligament (TCL) (106), placed first under the guidance of the curved cannulated guide rod (28).

In its preferred embodiment, there is also, close to the distal end of the cannula, an arch-brake (37) which helps: a) to restrain the final progression of the blade portion (21) of said fasciotome (25), being another element preventing the blade from deviating forwards or upwards, towards the palm of the hand, as illustrated in FIG. 14; b) to push aside soft tissues underneath the TCL, and c) to enhance the surgeon's tactile sense of the under surface of the TCL. At the open distal end, there are a couple of handles or ears (38) to facilitate its handling, as illustrated in FIG. 17.

405—Proximal edge of the transverse carpal ligament (TCL);
405A—Antebrachial fascia (Palmar carpal ligament) (PCL);
810—Wire.

Figure 8A:
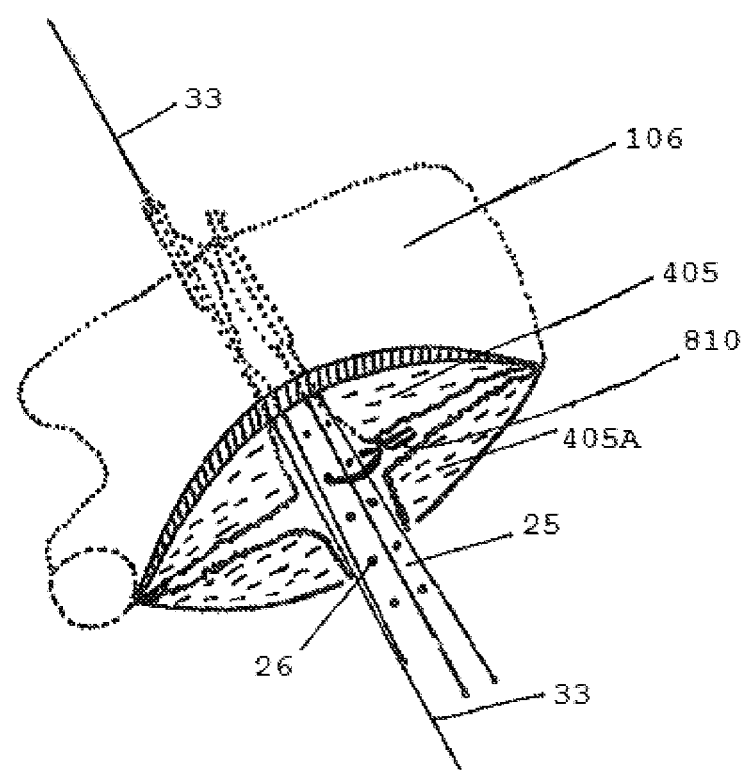
Figure 8B:
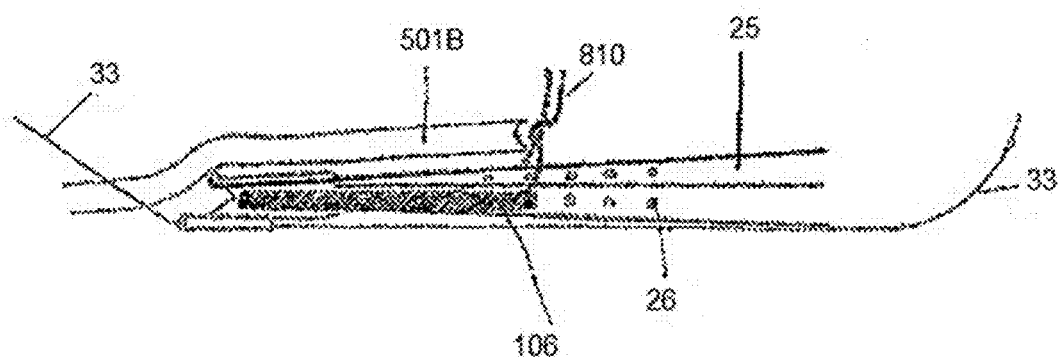
Figure 8C:
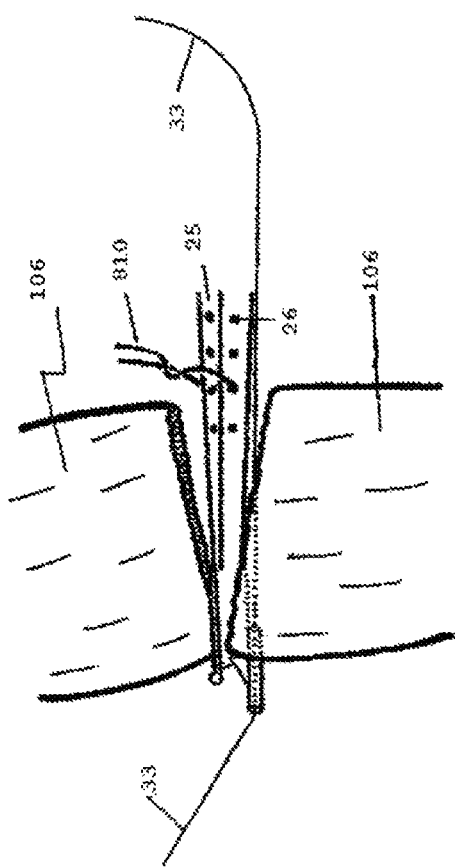

FIG. 8A is a schematic view of a human palm and wrist illustrating the complete division of the transverse carpal ligament (TCL) by the progression of the transverse carpal ligament (TCL) fasciotome, under guidance of the flexible metal guide needle, along the entire length of the ligament (TCL), in which numbers represent the same as indicated under FIG. 8C.

FIG. 8B is a larger scale view of a portion of FIG. 8A showing a sagital plane view of the same described procedure, the cut of the transverse carpal ligament (TCL), in which numbers represent the same as indicated under FIG. 8C.

FIG. 8C is a larger scale view of a portion of FIG. 8A showing a transverse plane view of the same described procedure, the cut of the transverse carpal ligament (TCL), in which numbers represent the following:
25—Fasciotome;
26—Fenestrations in the fasciotome shaft;
33—Flexible metal guide needle;
106—Transverse carpal ligament (TCL);
810—Wire;
405A—Antebrachial fascia (Palmar carpal ligament);
501B—Skin.

Figure 9A:
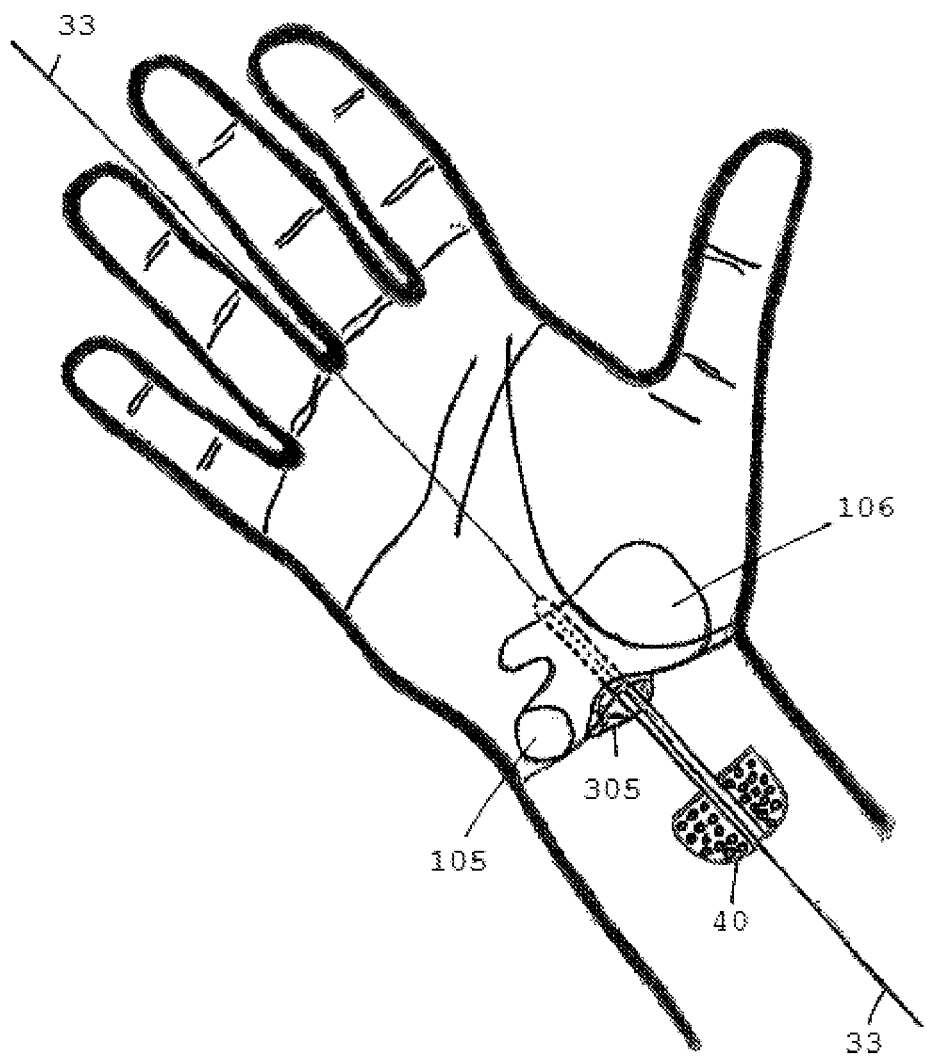
Figure 9B:
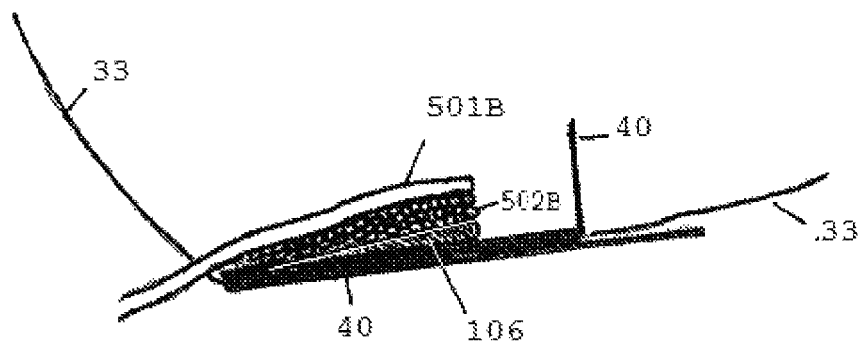
Figure 9C:
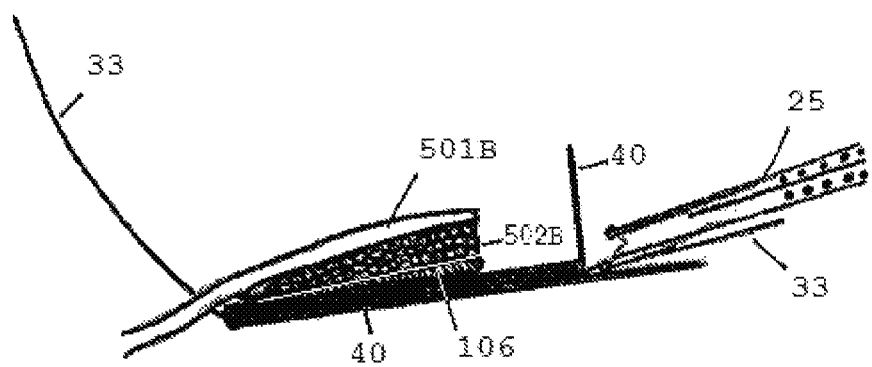
Figure 9D:
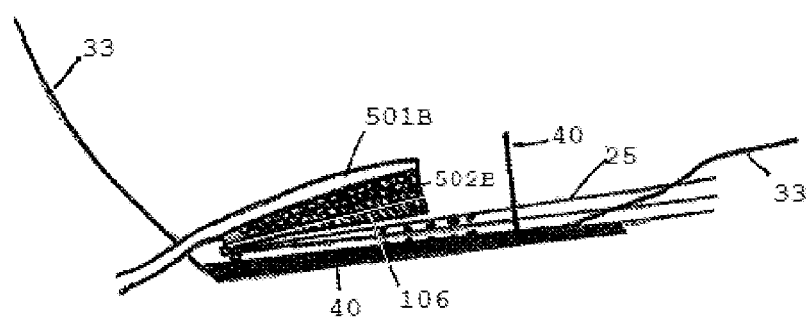

FIG. 9A is a schematic view of a human palm and wrist illustrating the use of the optional slotted, fenestrated tip, guide cannula which is part of the invention described herein, introduced underneath the transverse carpal ligament (TCL), under the guidance of the flexible metal guide needle introduced through its fenestrated tip, in which numbers represent the same as indicated under FIG. 9D.

FIG. 9B is a larger scale view of a portion of FIG. 9A, illustrating a sagital plane view of the same procedure, the fully introduction under the transverse carpal ligament (TCL) of the slotted, fenestrated tip, guide cannula until it is prevented from progressing further by the flexible metal guide needle abutting against the deep surface of the palmar skin, in which numbers represent the same as indicated under FIG. 9D.

FIG. 9C shows the same plane view as FIG. 9.B, illustrating the surgical step that follows in the procedure which is the subject hereof, consisting of the initial introduction of the transverse carpal ligament (TCL) fasciotome along the flexible metal guide needle lying along the longitudinal slot of the slotted, fenestrated tip, guide cannula, in which numbers represent the same as indicated under FIG. 9D.

FIG. 9D shows the same plane view as FIG. 9C with the transverse carpal ligament (TCL) fasciotome fully introduced along the longitudinal slot of the slotted, fenestrated tip, guide cannula, along the sectioned transverse carpal ligament (TCL), in which numbers represent the following:
25—Fasciotome;
33—Flexible metal guide needle;
40—Slotted Fenestrated Tip Guide Cannula;
105—Pisiform bone;
106—Transverse carpal ligament (TCL);
305—Surgical Incision;
501B—Skin;
502B—Subcutaneous fat.

FIG. 10 is 3D view of a preferred form of embodiment of the curved tip cannulated guide rod, which is part of the invention described herein, with a "nail" at the tip of the shaft coupled to a suitable form of rear handle in which numbers represent the following:
27—Handle (of the) curved tip cannulated guide rod;
28—Cannulated rod shaft;
29—Curved distal end of the cannulated rod;
30—Tooth or nail.

Figure 11B:
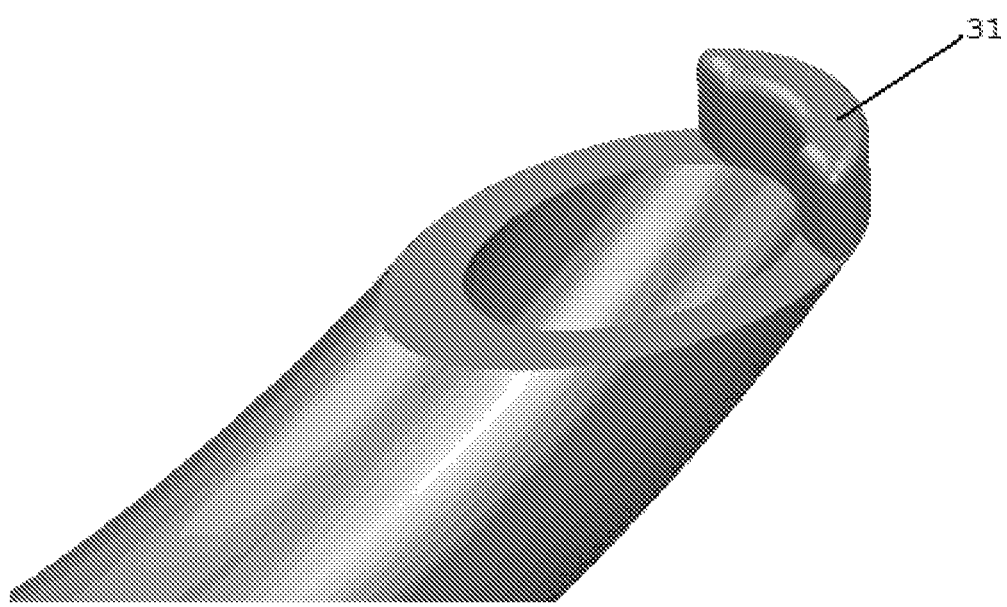

FIGS. 11A and B are larger scale 3D views of a portion of FIG. 11, highlighting the tip of the curved tip cannulated guide rod, in two of the preferred forms of embodiment, with a "tooth" or a "nail" at its distal end, in which numbers represent the following:
30—Tooth;
31—Nail.

Figure 12:
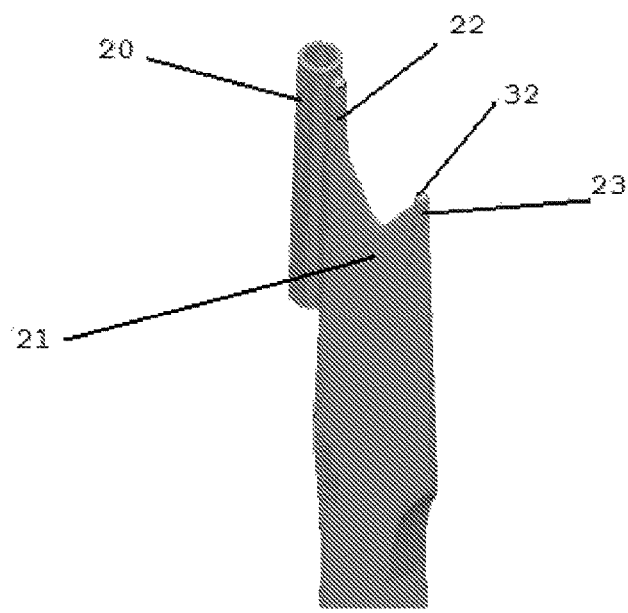

FIG. 12 is a 3D view of one of the preferred forms of embodiment of the distal end of the straight shaft fasciotome which is part of the invention described herein, in which numbers represent the following:
20—Canulated finger-like prong;
21—Blade (knife cutting edge);
22—Inferior finger-like prong;
23—Superior finger-like prong;
32—Metal sphere.

Figure 13:
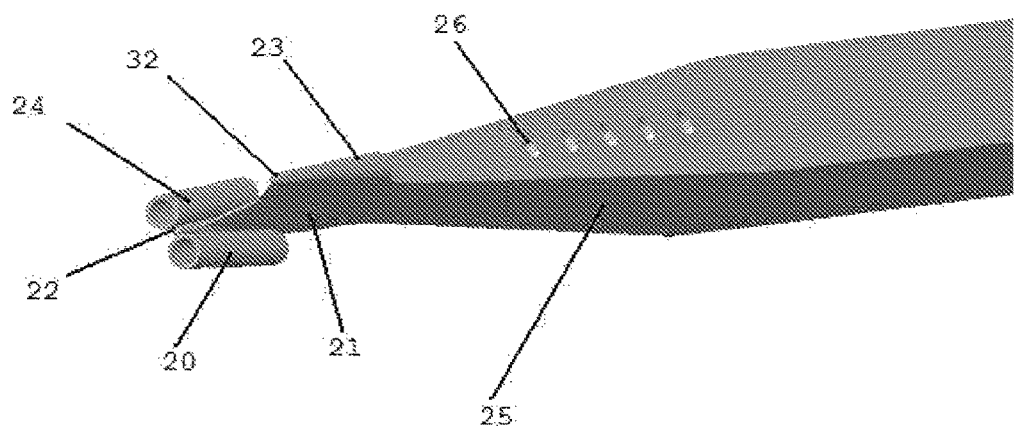

FIG. 13 is a 3D view of another preferred form of embodiment OF the distal shaft and end of the transverse carpal ligament (TCL) fasciotome which is part of the invention described herein, issuing two parallel cannulated finger-like prongs, in which numbers represent the following:
20—Canulated finger-like prong;
21—Blade (knife cutting edge);
22—Inferior finger-like prong;
23—Superior finger-like prong;
24—Canulated finger-like prong;
25—Fasciotome;
26—Fenestrations in the fasciotome shaft;
32—Metal sphere.

Figure 14:
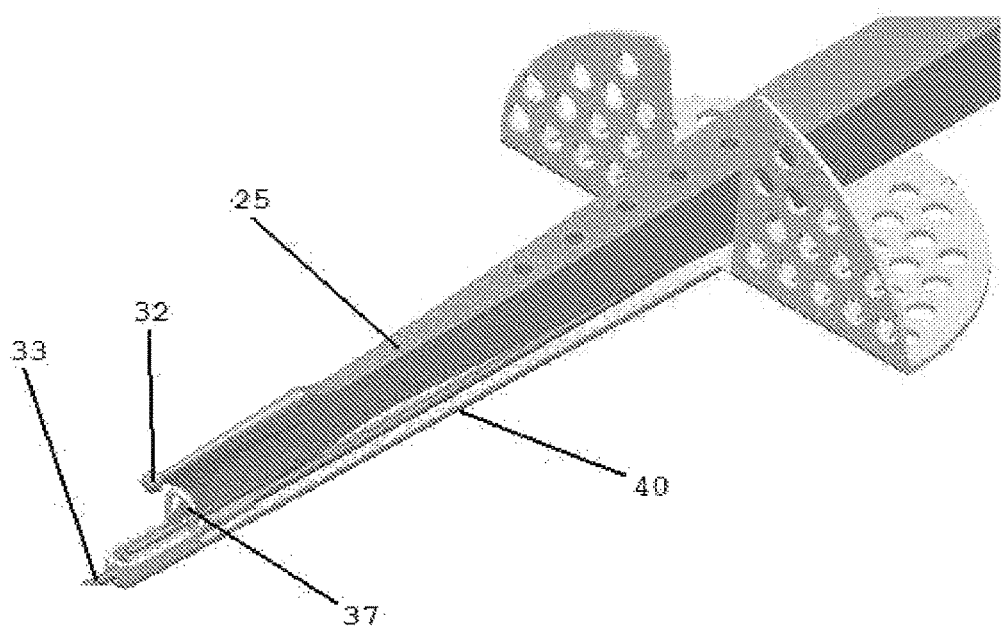

FIG. 14 is a, distal to proximal, 3D view of the assembly consisting of the flexible metal guide needle used in the procedure which is the subject hereof, the slotted, fenestrated tip, guide cannula and the transverse carpal tunnel cutting knife or fasciotome, in a preferred form of embodiment, with a metal sphere at the tip of the superior distal finger-like prong in the head portion of the fasciotome that are, both, part of the invention described herein, in which numbers represent the following:
25—Fasciotome;
32—Metal sphere;
33—Flexible metal guide needle;
37—Restraining metal arch or arch-brake;
40—Slotted Fenestrated Tip Guide Cannula.

Figure 15:
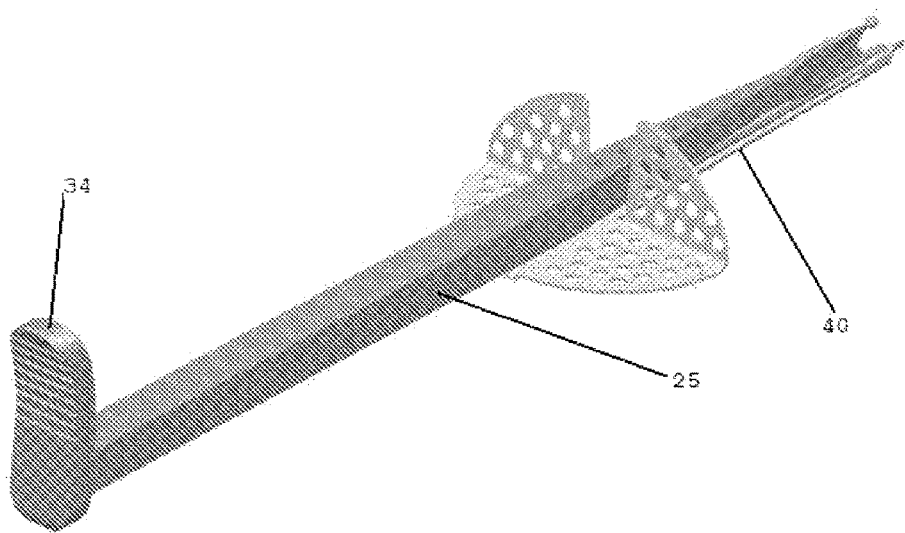

FIG. 15 is the same, proximal to distal, 3D view of the assembly shown in FIG. 14, illustrating the preferred form of embodiment of the rear handle of the straight shaft carpal tunnel cutting knife or fasciotome, which is part of the invention described herein, in which numbers represent the following:
25—Fasciotome;
34—Rear handle;
40—Slotted Fenestrated Tip Guide Cannula.

Figure 16:
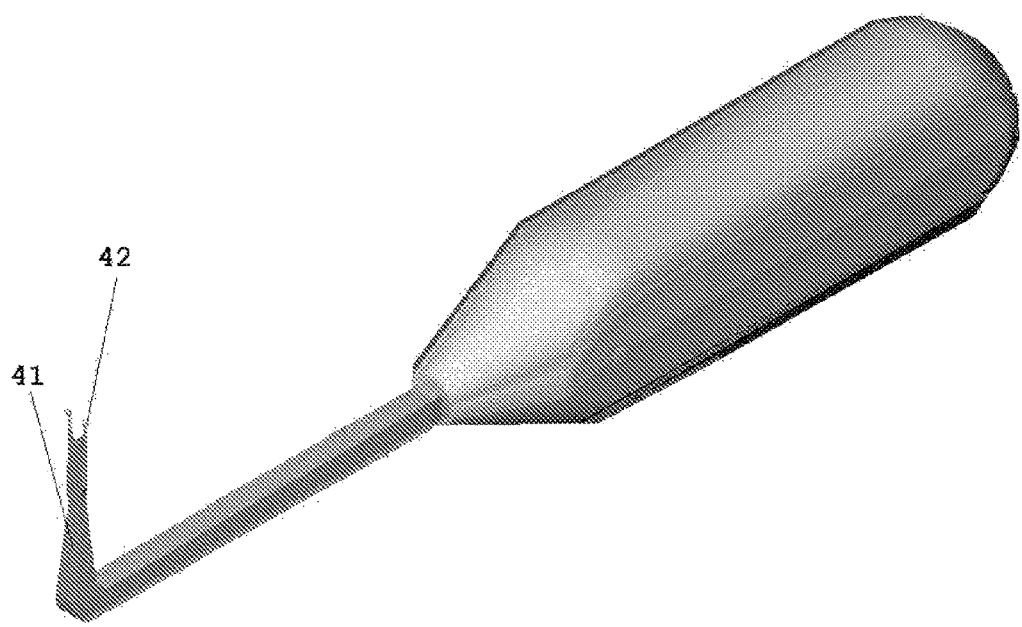

FIG. 16 is a distal to proximal, 3D view, of the 90° curved shaft fasciotome that is part of the invention described herein, coupled to a suitable form of rear handle, in which numbers represent the following:
41—90° angled shaft fasciotome;
42—Metal sphere.

Figure 17:
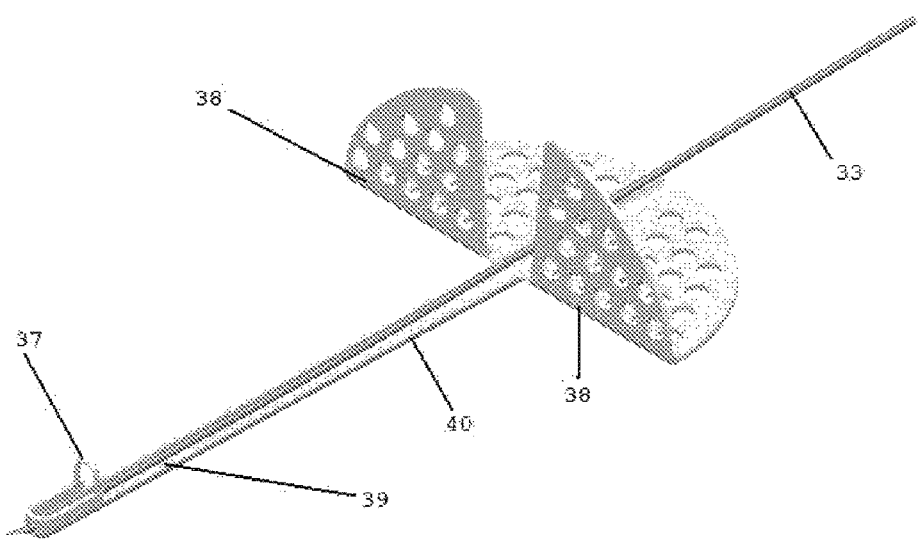

FIG. 17 is a, distal to proximal, 3D view of the assembly consisting of the flexible metal guide needle used in the procedure which is the subject hereof, placed along the longitudinal slot of the slotted fenestrated tip guide cannula, which is part of the invention described herein, with its tip protruding through the fenestrated closed distal end of the cannula. The restraining metal arch at the distal dorsal shaft of the cannula is also illustrated. The numbers represent the following:

33—Flexible metal guide needle;
37—Restraining metal arch or arch-brake;
38—Ears/Handles;
39—Longitudinal slot;
40—Slotted Fenestrated Tip Guide Cannula.

Figure 18:
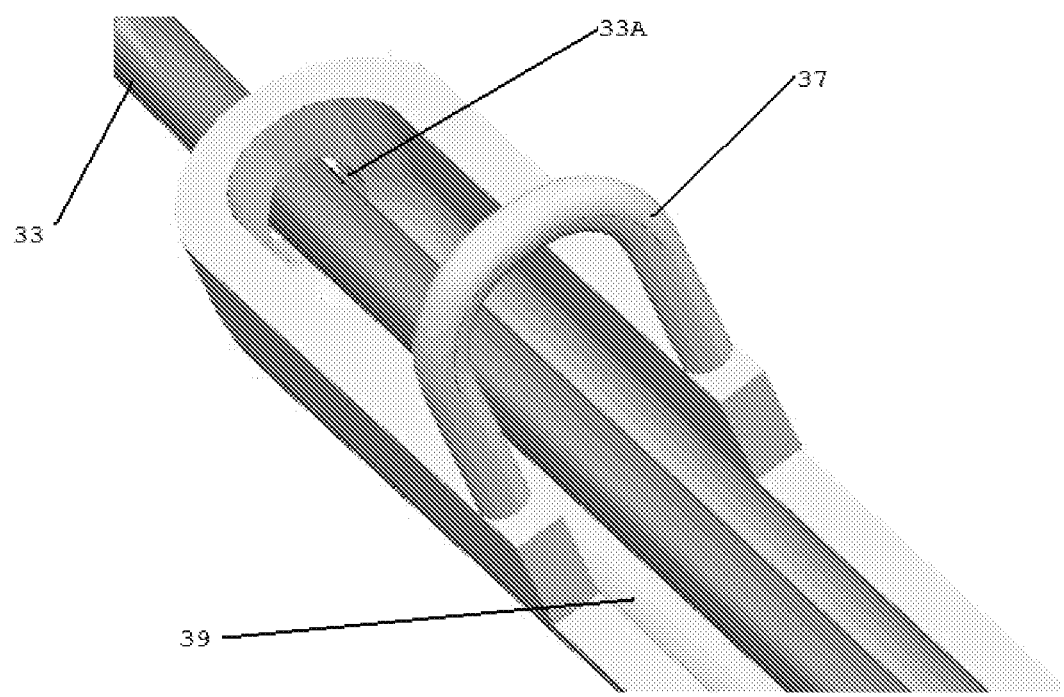

FIG. 18 is a larger scale, proximal to distal, 3D view of the distal end assembly consisting of the flexible metal guide needle used in the procedure which is the subject hereof, placed along the longitudinal slot of a preferred form of embodiment of the slotted, fenestrated tip, guide cannula that is part of the invention described herein with its tip protruding through the fenestrated closed distal end of the cannula. The restraining metal arch at the distal dorsal shaft of the cannula is also illustrated. The numbers represent the following:

33—Flexible metal guide needle;
33A—Front hole of the Slotted fenestrated Tip Guide Cannula;
37—Restraining metal arch or arch-brake;
39—Longitudinal slot.

Figure 19:
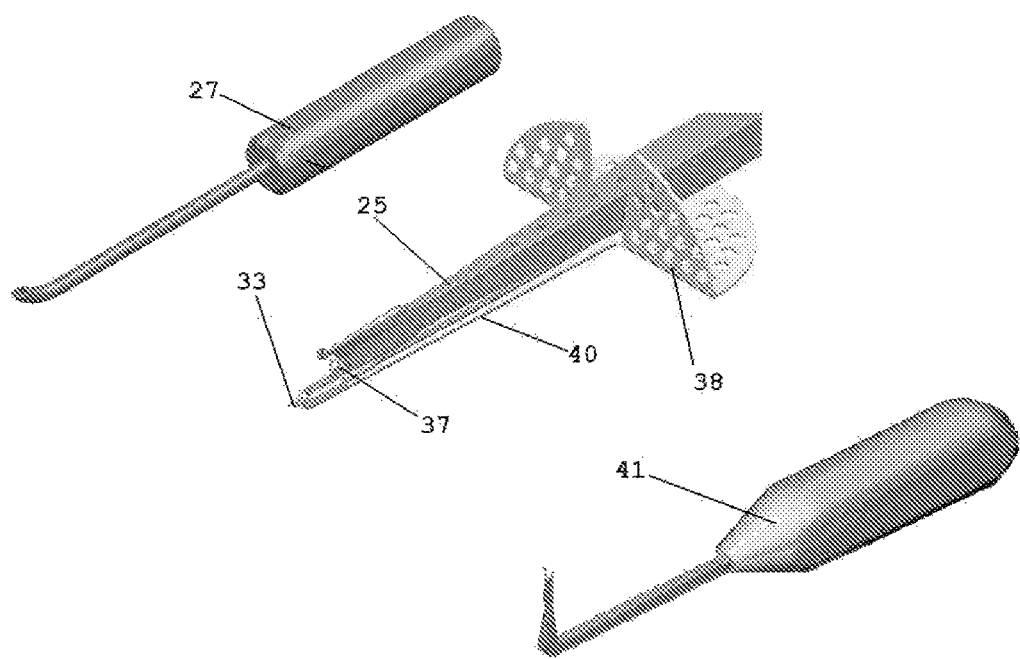

FIG. 19 is a, distal to proximal, 3D view of the assembly of instruments that are part of the invention described herein, namely, from left to right: the cannulated guide rod, the transverse carpal ligament cutting knife or fasciotome on the slot of the slotted fenestrated tip guide cannula and the cutting knife or fasciotome with a 90° curved shaft, in which numbers represent the following:

25—Fasciotome;
27—Handle (of the) curved tip cannulated guide rod;
33—Flexible metal guide needle;
37—Restraining metal arch or arch-brake;
38—Ears/Handles;
40—Slotted Fenestrated Tip Guide Cannula;
41—90° angled shaft fasciotome.

DETAILED DESCRIPTION OF THE INVENTION

The present invention discloses a set of surgical instruments particularly, but not exclusively, suited for cutting the transverse carpal ligament (TCL) during carpal tunnel surgery and its method of use, comprising:

A cannulated guide rod (28) having, preferably, a cylindrical section and two open ends, with a curved distal extremity (29). Its lumen allows the introduction of a flexible metal guide needle (33), the guide for the blade portion of the carpal ligament cutting knife or fasciotome (25). The instrument is characterized by having an appropriate size and shape in order to optimize its introduction into the palm, underneath the under surface of the transverse carpal ligament (TCL), through a minimal surgical incision, and also leading the introduction of the said guide needle (33) to a selected point in the palm of the hand.

In addition, the said rod (28) is characterized by having, about 1 cm from its distal end, a buckle (29) with an angle, of about 25° to 30°, in order to: facilitate its introduction below the under surface of the TCL; push upwards with its tip the under surface of the TCL; enhancing the surgeon's tactile sense of said ligament and of its distal edge and leading the tip of the flexible guide needle (33) upwards in the direction of the surface of the palm of the hand, so that the tip of the needle will extrude at a point in the palm near the tip of said rod.

In one preferred form of embodiment, said rod (28) is still characterized by having attached to the tip of the most distal border of its curved end, in the side of the convexity, a protrusion, like a tooth (30) or nail (31), of, at least, 1 mm high, as presented in FIGS. 11-A and 11-B, facilitating and enhancing the surgeon's tactile sense of the under surface of the TCL, plus inducing a sense of a jerk when the distal edge of the ligament is exceeded. As part of the measures conceived to avoid an incomplete cut of the TCL, on the distal superior surface of the shaft (28), considered to be the side of its concavity, it may be engraved, by one of several means known in the art, a metric scale (607) for the double purpose of referencing at all times to which direction the tip of the rod is pointing and to determine the length of the device inserted into the palm, as presented in FIG. 10.

Said rod must be manufactured, by one of several means known in the art, with biocompatible metal, such as surgical stainless steel or iron-based, titanium-based, cobalt based or any other suitable alloy, with the following preferred dimensions, which may be altered for manufacturing purposes or for adjustment to the ergonomic conditions of the surgeon:

Length: 50 to 100 mm
External diameter: 3-5 mm
Inside diameter: 2-3 mm

This cannulated guide rod (28) may be couple with any type of handle as it may be convenient for manufacturing and for the surgeon to control and maneuver the instrument. Said handle can be manufactured, by one of several means known in the art, preferably with either a metallic alloy of the same sort of the rod or a biocompatible material resistant to high temperatures, e.g., high density polyethylene or other of the family of plastics.

In any case it is critical that the proximal end of the rod (28) be always visible and permeable on the side of the handle to allow for the insertion of the flexible metal guide needle (33) into the lumen of the instrument.

The proposed set of this invention included also a cutting knife or fasciotome (25) comprising at least a cannulated, tubular, finger-like prong (20 or 24) which can be coupled to a finger-like solid prong (22) present at the bottom surface of the cutting blade (21) or, alternatively, may even replace it, if the lower end of the blade holder, in a preferred form of embodiment, is manufactured flat or with a flattened shape, rounded at its tip, allowing for the direct fixation to it of said cannulated tubular prong (20). The purpose of said cannulated, finger-like, prong (20) is to lead the passage of the flexible metal guide needle (33) after this one has been positioned in place with the help of the cannulated guide rod (28). This needle will guide the progression of the blade portion (21) of said knife or fasciotome, during the cutting action, eliminating the possibility of the device to deviate from the intended route into any wrong passageway.

Said fasciotome is also characterized by having, in one preferred form of embodiment, attached to the tip of the upper finger-like solid prong (23) a metal sphere (32), with the preferred size of 2 mm, placed preferably eccentrically in order not to decrease the width of the blade portion (21). This sphere (32) also increases security, by enhancing the bluntness of said solid finger-like prong (23), virtually eliminating the possibility of the blade (21) to deviate from the intended route into any wrong passageway, namely downwards, across the transverse carpal ligament (106), towards the median nerve and tendons. However, its preferred size does not interfere with forward advancement of the fasciotome. Said fasciotome also presents, in a preferred form of embodiment, in the distal part of the fasciotome shaft (25) in, at least, two of its sides or edges, a group of fenestrations (26), placed at regular, referenced, distances from each other and from the tip of the instrument, forming a scale that the surgeon can use to verify the length of the devise that has been advanced into the hand and, therefore, the length of the cut performed in the TCL (106).

Said fasciotome also includes a handle (34), FIG. 15, in order to make it easier to push the instrument through the ligament. This cutting knife or fasciotome (25) may be manufactured, by one of several means known in the art, with biocompatible material, in two different forms: "disposable" and "non-disposable" or "permanent", in the preferred form of embodiment:

1) The "disposable" fasciotome consists of a forward or distal blade portion made of stainless steel or any other biocompatible, high strength, metal alloy coupled with a disposable shaft and rear handle, manufactured, by one of several means known in the art, with a biocompatible material resistant to high temperatures, e.g., high density polyethylene or other of the family of plastics.

2) The permanent or "non-disposable" fasciotome is manufactured, by one of several means known in the art, as a fully metallic piece, made of surgical stainless steel or any other biocompatible, high strength metal alloy, like the ones described for the cannulated guide rod (28).

The remaining structural parts of the cutting knife/fasciotome (25) and their preferred dimensions, which may be altered for reasons of convenience of industrial manufacture or to fit the ergonomic characteristics of the surgeon, without that meaning that we are facing a new instrument, follow:

Rear Handle

Trapezoid-shaped, with a major longitudinal axis, concave-convex, with the concavity facing away from the shaft, crossed transversely by a set of bas relief indentations (grooves or slots) across its entire width.

Recommended Dimensions:
Length: 29 mm
Width: 10 mm
Thickness: 5 mm
Indentations on the concave surface of the handle, away from the stem: 1 mm deep (bas relief).
CONNECTION TO THE SHAFT OR STEM—mounted perpendicularly to it, on the rearward end of said shaft, in a way that its lower transverse side does not protrudes more than roughly 5 mm below the inferior surface of said shaft and this configuration allows to fulfill the following objectives:

1) To provide a comfortable surface and functional support for the thumb to push the fasciotome (25) along the TCL during the cutting action.

2) To have an ergonomic configuration, adapting to the convexity of the palm side of the thumb.

3) The indentations contribute to the stability of the instrument by increasing the adhesion/friction between the device and the gloved thumb during the surgery.

4) The detail of the cable being attached to the stem in the manner described, eccentrically upwards, prevents the handle from impinging on the palmar surface of the forearm of the patient while pushing the fasciotome (25) forward, towards the hand, therefore, not hindering the progression of the instrument during the process
of cutting the TCL.
Shaft or Stem
Proximal (Rear) End
In a preferred form of embodiment, with a square section, with the following recommended side dimensions: 6 mm
Diaphysis
In its preferred form of embodiment, with a square proximal section, in continuity with the proximal (rear) end roughly 100 mm away from the rear end, the diaphysis tapered gradually towards its distal end and assuming a pyramidal form, preferentially flattened in the transverse axis, becoming with greater height than width. Recommended dimensions (diaphysis only):

Length: 130-140 mm
Proximal width up to 100 mm away from the rear end: 6 mm side, preferably with a square configuration.
Tapering of the stem from this point onwards, until it reaches the dimensions of 4 mm in the vertical axis at the stem's neck, at 140 mm distance from the rear of the device and 25 mm proximal to the tip of the device.
Progressive narrowing of the stem from the same point to 2 mm in the transverse axis, at the level of the neck of the stem, at 140 mm distance from the rear of the device and 25 mm proximal to the tip of the device.

The shaft is fenestrated along its vertical, horizontal or both sides, for a preferred number of five holes, arranged at equal distances between them, preferably 5 mm, starting 30 mm away from the cutting edge of the blade of the distal end and ending at 50 mm. In one preferred form of embodiment, a numerical scale may be engraved next to the holes (26), in the form of laser marks or any other known in the art.

Distal (Foreward) End (Blade Portion; Blade)
This extremity consisting of a head portion consisting of:
1) A blade, trapezoidal, attached to the opposite end of the head portion, with the sharp distal cutting edge preferably concave or "V" ("fish mouth") shaped, with the following recommended dimensions:

Maximum length: 14 mm
Length at the concavity (rearmost point): 10 mm
Height: 4 mm
Width: 1 mm It is recommended that the sharp distal cutting edge is moderately but not overly sharp, in order to cut easily through the TCL (106), but with a certain degree of resistance, enhancing the surgeon's tactile sense of the cut being performed.

2) a solid, blunt finger-like prong, attached to the superior edge of the blade, in continuity with the shaft's neck, with the following preferred dimensions:

Maximum length: 10 mm
Diameter: 1 mm

The tip of this finger-like prong should preferably extend beyond the apex of the concavity of the blade by, at least, 4 mm. In its preferred form of embodiment, a metal sphere (32) with roughly 2 mm in diameter is attached to its tip, placed preferably eccentrically outwards, in order not to decrease the width of the blade portion.

3) a solid, blunt finger-like prong, attached to the inferior edge of the blade, in continuity with the shaft's neck, with the following preferred dimensions:

Maximum length: 13 mm
Diameter: 1 mm

This prong should preferably extend beyond the apex of the concavity of the blade of about 6 mm, projecting therefore, ahead of its similar.

4) a cannulated finger-like prong, attached to said inferior, solid, blunt finger-like prong or, alternatively, replacing it entirely, attached directly to the bottom surface of the blade, with the same dimensions and position characteristics of the solid cylinder in continuity with the shaft's neck, and, in a preferred form of embodiment, also with a beveled distal end, with the bevel oriented from superior to inferior and front to back and with the following preferred dimensions:

Maximum length: 13 mm
Outside Diameter: 2 mm
Internal Diameter: 1 mm
Preferably beveled distal end Another three keys features of the head portion of the fasciotome (25) are the following: 1) the width between the inferior surface of the two solid finger-like prongs (22; 24), bound to each side the blade (21), is on the order of about 4 mm because we have found that the thickness of the transverse carpal ligament may exceeds 3 mm in adults. The 4 mm span, therefore, prevents impingement of said prongs on the ligament which could prevent the unimpaired progress of the knife through the ligament during the cutting process. Another, 2), is that the length of the superior solid finger-like prong (23) does not need to extend roughly more than 4 mm in relation to the most distal edge of the blade (21) because, specially if a metal sphere (32) is coupled to the tip of the prong, as recommended in one preferred form of embodiment, that is enough to prevent any misguidance of the device. 3) Likewise, the length of the inferior finger-like cannulated prong (20; 24) does not need to extend roughly more than 6 mm in relation to the most distal edge of said blade (21) because, during the process of cutting the transverse carpal ligament (TCL) (106), the instrument is orientated along the entire extent of the cut by the flexible metal guide needle (33) introduced in said cannulated finger-like prong and not by the prong itself. The reduced protruding length of the prongs helps to prevent any possible jamming of the head portion of the instrument against the tissues.

Cutting Knife or Fasciotome with a 90° Angle Curved Shaft (41) (FIG. 16)

This cutting knife or fasciotome (41) may be manufactured, by one of several means known in the art, with biocompatible material, in two different forms: "disposable" and "non-disposable" or "permanent".

1) The "disposable" fasciotome consists of 1) a forward or distal blade portion made of surgical stainless steel or any other biocompatible, high strength metal alloy, like the ones described for the cannulated guide rod (28) manufactured by one of several means known in the art, without that meaning that we are facing a new instrument, attached to 2) a disposable rear handle and/or rear shaft, manufactured by one of several means known in the art, with a biocompatible material resistant to high temperatures, e.g., high density polyethylene or other of the family of plastics. The rear handle may have any size or shape fitting the ergonomic characteristics of the surgeon and/or the convenience of the industrial manufacturing, without this meaning that we are faced with a new instrument.

2) The permanent or "non-disposable" fasciotome may be manufactured, by one of several means known in the art, 1) as a fully metallic piece, made of surgical stainless steel or any other high strength metal alloy, like the ones described for the cannulated guide rod (28) or 2) to have the same characteristics as the ones described for the disposable fasciotome, with the difference that the biocompatible, plastic or other non-metal, material must have the capacity to withstand high temperatures repeatedly, as happens during repeated sterilization processes.

Structural Parts and Preferential Dimensions:

The remaining structural parts of the cutting knife/fasciotome (41) and their preferred dimensions, which may be altered for reasons of convenience of industrial manufacture or to fit the ergonomic characteristics of the surgeon, without that meaning that we are facing a new instrument, follow:

Shaft or Stem

Proximally with a 90° degree angle bend, it may be attached to any sort of appropriate handle, as previously described herein, with the following preferred dimensions and morphological characteristics:

Until the angle of curvature: parallelepiped shaped and quadrangular section and the following preferred dimensions:

Length: 30 a 60 mm

Height and width: 5 mm

After the angle of curvature: of pyramidal shape and proximal quadrangular section, in continuity with the preceding portion of the rod, tapering towards its distal end, assuming a pyramid shape, flattened in the transverse axis, with greater height than width, with the following preferred dimensions:

Overall length: 30 to 50 mm

Height: at the bend angle: 3 to 5 mm; at the distal end: 2-3 mm

Width: at the bend angle: 3 to 5 mm; at the level of the distal end: 1-2 mm

Distal (Head; Forward) End/(Blade Portion; Blade)

This extremity consisting of:

1) A blade holder with two finger-like solid prongs (22; 23) at the tip, extending forwardly above and below the blade, symmetrically, for a distance, in one preferred form of embodiment, of roughly 6 mm in relation to the most distal edge of the blade. Alternatively, the lower end of the blade may be flat or rounded at the end, extending below the blade for the same distance.

2) A blade, trapezoidal (FIG. 12), attached to the opposite end of the head portion, contained in between the two prongs mentioned above, with the sharp distal cutting edge preferably concave or "V" ("fish mouth") shaped, with the following recommended dimensions:

Maximum length: 14 mm

Length at the concavity (rearmost point): 10 mm

Height: 2-3 mm

Width: 1-2.5 mm

It is recommended that the sharp distal cutting edge is moderately but not overly sharp, in order to cut easily through the antebrachial fascia (405A), but with a certain degree of resistance, helping the surgeon to have the feeling of the cut that he is performing.

3) At the tip of each finger-like prong it is attached, in one preferred form of embodiment, a metal sphere (42), with the preferred size of roughly 2 mm, placed preferably eccentrically outwards, in order not to decrease the width of the blade portion. Alternatively, they can be attached centrally on the tip of the prong, as long as the span between them is at least 2 mm. This width is not as critical as in the case of the straight shaft transverse carpal fasciotome (25) because the purpose of this knife is to cut blindly through the distal antebrachial fascia, which is not thicker than 1 mm in adults. Therefore a blade width of 2 to 3 mm is appropriate for this instrument.

The purpose of said spheres is to increase the bluntness of the tip of the prongs surrounding the blade, making it virtually impossible for the instrument to cut through the fascia in another direction other than the one planed (vertically upwards, parallel to the longitudinal axis of the forearm).

Guide Cannula (40) (FIG. 17)

A guide cannula (40) with a closed but fenestrated distal end and an open proximal end, the cannula provided with a longitudinal slot (39) extending from a point adjacent to the cannulated distal end to a point adjacent to the open proximal end. The cannula can have a C or D-shaped interior cross-section with the flat part of the C or D—shape lying along the rim of the longitudinal slot.

This slotted, fenestrated end tip, guide cannula is a modification of a common slotted probe-cannula, as described below:

a) Includes a fenestration—circular hole (33A)—at the front end of the cannula, in the preferred form of embodiment, with roughly 1.5-2 mm in diameter, to allow the passage of the flexible metal guide needle (33) already mentioned herein.

b) In one preferred embodiment, there is also a restraining metal arch or arch-brake (37) extending roughly 2 mm above the level of the inner rim of the cannula, with a diameter of roughly 1 mm and attached roughly 3 mm proximal to the inner rim of the distal end of said cannula. This arch-brake helps in pushing aside soft tissues underneath the transverse carpal ligament (106) during the insertion of said cannula (40) and enhances the manual sensitivity of the surgeon to the under surface of said ligament (106). It also helps restraining the final progression of the blade (21) of said fasciotome (25), being another element preventing the blade from unwanted deviations towards the palm.

c) At the open distal end of said cannula (40), there are attached a couple of 2 end-side handles (38), each with the overall shape of a semi-circle bent in the middle at 90° angle, forming two L shaped leaves, of which the horizontal one is attached to said shaft of said cannula, with the preferred dimensions of roughly 25 mm tall by 25 mm wide and, in a preferred form of embodiment, fenestrated with multiple round holes, like a network. The L shaped configuration allows a comfortable and safe grip of the instrument with any of the operator's hands. The "network" morphology significantly decreases the weight of the piece; the multiple fenestrations make the instrument lighter.

Operative Procedure

An explanation of the operative technique, including the inventive aspects of the method and devices disclosed herein is achieved by describing the method steps with reference to the drawings and the instruments.

Figure 1:
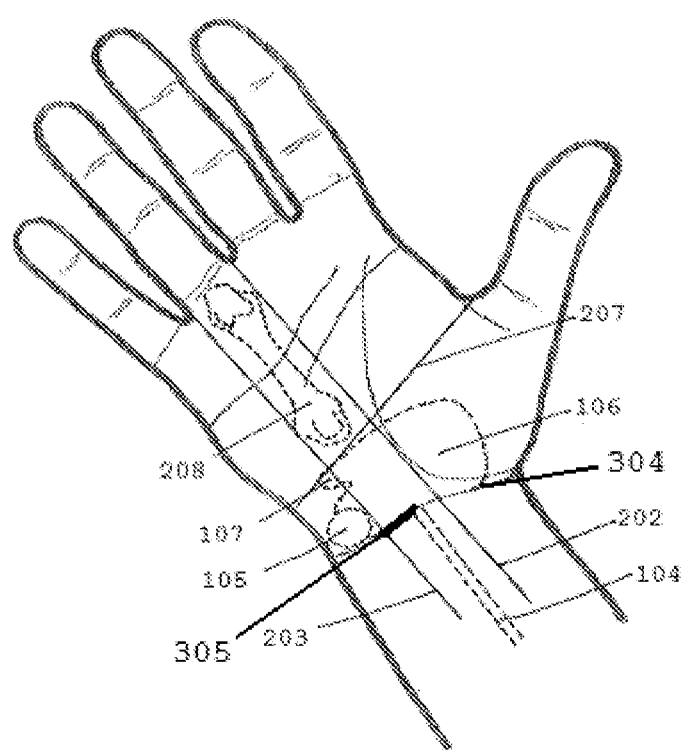
FIG. 1 is a schematic view of a human palm and wrist showing some anatomical structures and some of the landmarks plus the surgical incision used during the procedure described herein, in which numbers represent the following:
- 104—Tendon of Palmaris Longus Muscle;
- 105—Pisiform bone;
- 106—Transverse carpal ligament (TCL);
- 107—Hook of the hamate bone;
- 202—Line drawn as the continuation of the radial border of the ring finger;
- 203—Line drawn as the continuation of the ulnar border of the ring finger;
- 207—Kaplan's cardinal line;
- 208—4th metacarpal;
- 304—Distal wrist palmar crease;
- 305—Surgical Incision.

After the patient has been anaesthetised and the extremity properly prepared and draped, first, several landmarks are identified and marked as shown in FIG. 1, namely: 1) the pisiform bone (105) (where the proximal ulnar attachment of the transverse carpal ligament (TCL) lies); 2) the distal tendon of the Palmaris Longus muscle (104) at the level of the palmar distal wrist crease; 3) the cardinal line of Kaplan (207) and; 4) two lines (202; 203) as a continuation of, respectively, the radial and the ulnar borders of the ring finger. The cardinal line of Kaplan is drawn, as classically described, from the apex of the interdigital space between the thumb and the index finger, towards the ulnar side of the hand, parallel to the proximal palmar crease. The intersection of this line (207) with the line of continuation of the ulnar border of the ring finger (203) corresponds to the hook of the hamate (i.e. the distal ulnar attachment of the TCL). The area between the two ring finger's continuation lines (202) and (203) is considered to be a "safe zone" where the transverse carpal ligament (TCL) can be divided with a minimal risk for the underlying structures.

Figure 2:
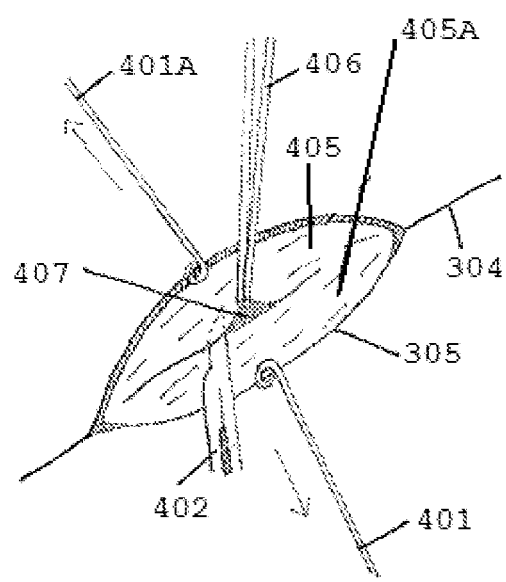
FIG. 2 is a schematic view of a human palm and wrist wrist showing the surgical incision in the skin, the skin edges being retracted by two skin hooks and a knife performing the transverse surgical incision in the wrist fascia used during the procedure described herein, in which numbers represent the following:
- 304—Distal palmar wrist crease;
- 305—Surgical Incision (skin edge);
- 401 and 401A—Skin hooks;
- 402—Knife (surgical blade);
- 405—Proximal edge of the transverse carpal ligament (TCL);
- 405A—Distal edge of the antebrachial fascia (palmar carpal ligament) (PCL);
- 406—Adson's forceps;
- 407—Surgical incision in the palmar fascia.

A, usually, one centimeter transverse incision (305) is made over the palmar distal wrist crease, starting one or two millimeters radial to the medial border of the Palmaris Longus tendon (104), whenever present, extending ulnarwards. Only the skin is cut sharply. This prevents causing any iatrogenic injury to underlying structures, namely, the superficial palmar branch of the median nerve radially and ulnar vessels and nerve medially. The skin is retracted with skin hooks as shown in FIG. 2 (401; 401A) and further dissection is carried out bluntly with fine dissecting scissors (not shown). Some subcutaneous fat and superficial fibbers of the antebrachial fascia are usually present. These are split and retracted (not shown). Any deeper fat bulging into the operative field is cut and removed to the extent necessary for clear visualization of the deep antebrachial fascia or palmar carpal ligament (not shown). Otherwise, the fat it is just retracted proximally and distally into the palm.

With the wrist slightly extended, the area corresponding to the junction of the distal edge of the palmar carpal ligament (405A) and the proximal edge of the transverse carpal ligament (405) is lifted with a pair of fine forceps (406) and is sectioned transversely and, optionally, also vertically, creating a diamond shaped defect, with an extension similar to the one made in the skin.

Figure 3:
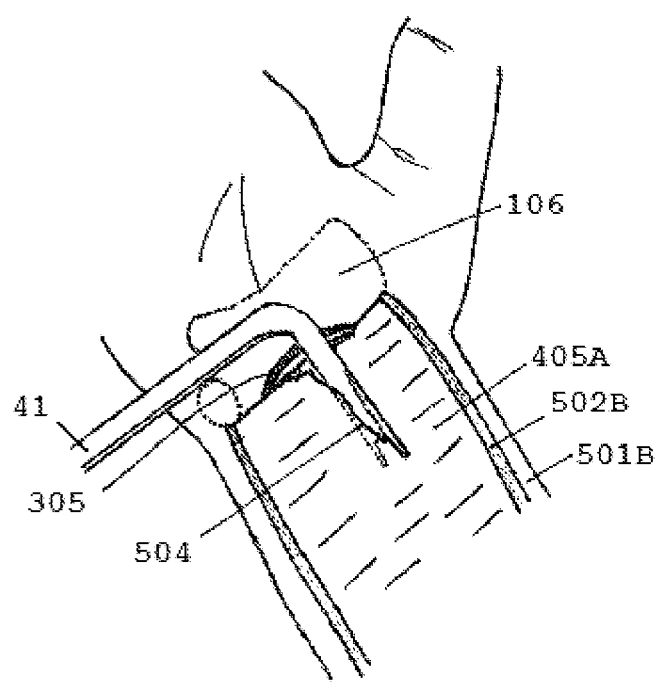
FIG. 3 is a schematic view of a human palm and wrist showing the 90° angled curved shaft fasciotome cutting the distal edge of the antebrachial fascia, during a part of the procedure described herein, in which numbers represent the following:
- 41—90° angled shaft fasciotome;
- 106—Transverse carpal ligament (TCL);
- 305—Surgical Incision;
- 405A—Antebrachial fascia (Palmar carpal ligament) (PCL);
- 501B—Skin;
- 502B—Subcutaneous fat;
- 504—Proximal cut in the distal antebrachial fascia.

A blunt curved dissector, e.g., MacDonald (not shown), is first passed proximally under the antebrachial fascia (405A) to separate any fascial adhesions, namely, of the median nerve to the said fascia, followed by a 4 mm diameter blunt rod, cannula inserter or round obturator (not shown) to further verify that a clear passage has been established. Once it is found that the above mentioned instruments can be passed freely into the proximal forearm, the 90° angle shaft fasciotome (41) is brought into the operative field and its cutting edge is positioned so that it straddles the distal palmar carpal ligament. The ligament is blindly cut for the extent of about two centimeters by pushing the knife proximally, parallel to the main axis of the forearm, as show in FIG. 3. There is no need for visual control of the cut as the two spheres (32) at the tip of the finger-like prongs (best seen in FIG. 16) prevent the knife from disengaging the ligament.

Figure 4A:
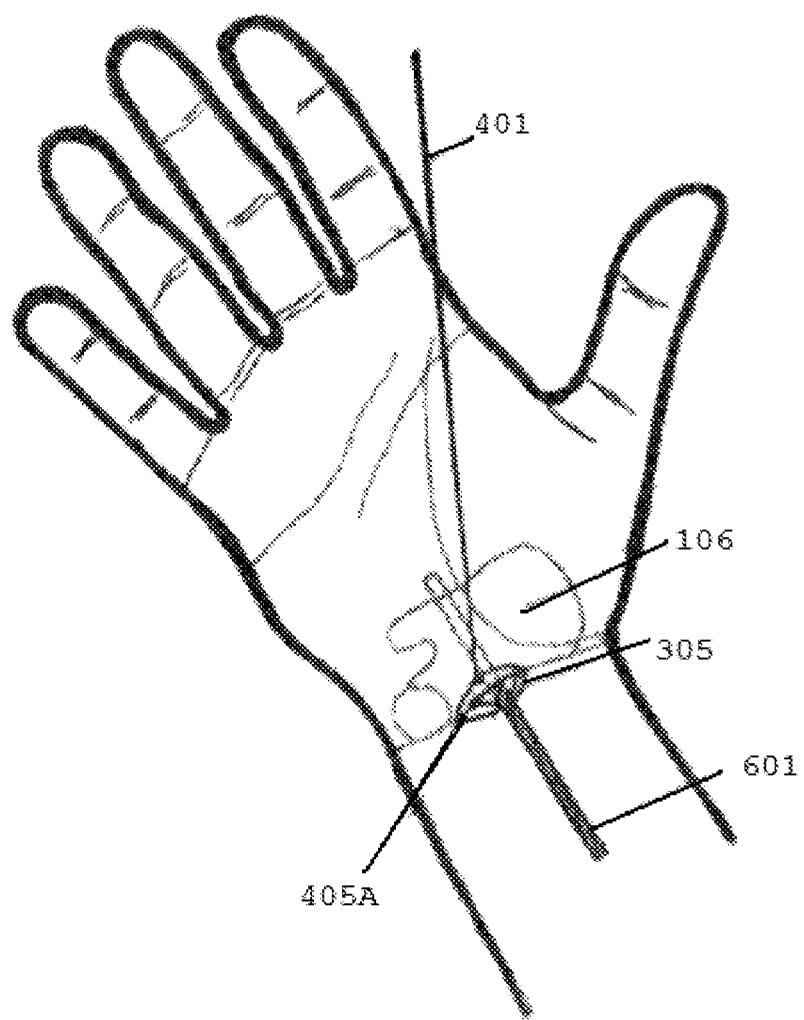
FIG. 4A is a schematic view of a human palm and wrist showing a blunt probe or obturator being introduced distally underneath the transverse carpal ligament (TCL) during a portion of the procedure described herein, in which numbers represent the same as indicated under FIG. 4.C.
Figure 4B:
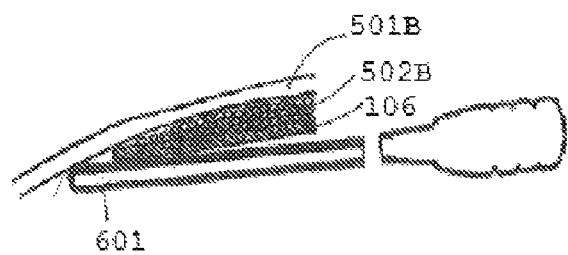
FIG. 4B is a larger scale view of a portion of FIG. 4.A showing a sagital view of the blunt probe or obturator introduced distally underneath the transverse carpal ligament (TCL), in which numbers represent the same as indicated under FIG. 4.C.

Next, the same manoeuvre is repeated distally. The blunt curved dissector and blunt rod (601) are passed under the TCL past the distal border of the ligament, as shown in FIGS. 4A and B, as it can be verified by the surgeons' manual feel of the position of the tip of the instrument under the ligament plus the protrusion of the same blunt tip in the area of the palm distal to the marked cardinal line of Kaplan (207). This feeling can be reinforced by digital pressure by the contra-lateral finger against the palm over the area of the protruding instrument (not shown).

Once the surgeon is reassured that the passage below the TCL (106) is free of adhesions, the curved tip cannulated guide rod (27) is passed in the very same way under the deep surface of said ligament in the "safe area" between said two lines extending proximally from the edges of the ring finger, to a point, more or less, 5 mm past the distal edge of the ligament, as shown in FIGS. 4A and C. This is to compensate the distance between the tips of the prongs of the straight shaft transverse carpal ligament fasciotome (25) and its cutting edge.

Figure 4C:
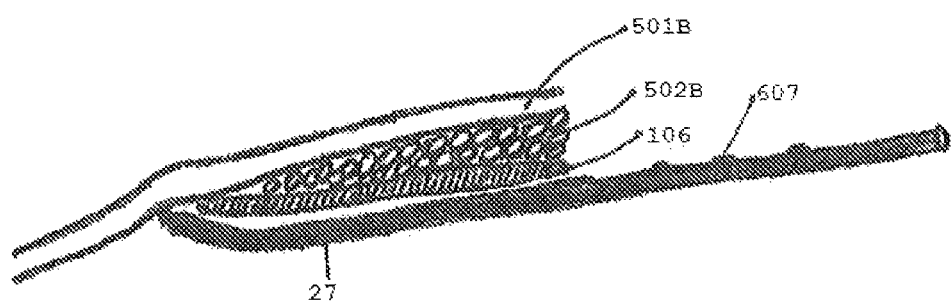
FIG. 4C shows the same sagital view as FIG. 4.B with the blunt probe or obturator replaced by the curved tip cannulated guide rod which is part of the invention described herein, in which numbers represent the following:
- 27—Curved tip cannulated guide rod;
- 106—Transverse carpal ligament (TCL);
- 401—Skin hook;
- 305—Surgical Incision;
- 405A—Antebrachial fascia (Palmar carpal ligament);
- 501B—Skin;
- 502B—Subcutaneous fat;
- 601—Blunt probe or obturator;
- 607—Laser marks of the curved tip cannulated guide rod.

The depth of the penetration of the guide rod (27) can be objectively calculated using the laser marks on the concave surface of the rod (607) (best seen in FIG. 4C). The surgeon must check what laser mark is closest to the distal edge of the surgical incision (305). These marks are also helpful indicating, at all times, in which direction the tip of the rod is pointing.

Figure 5A:
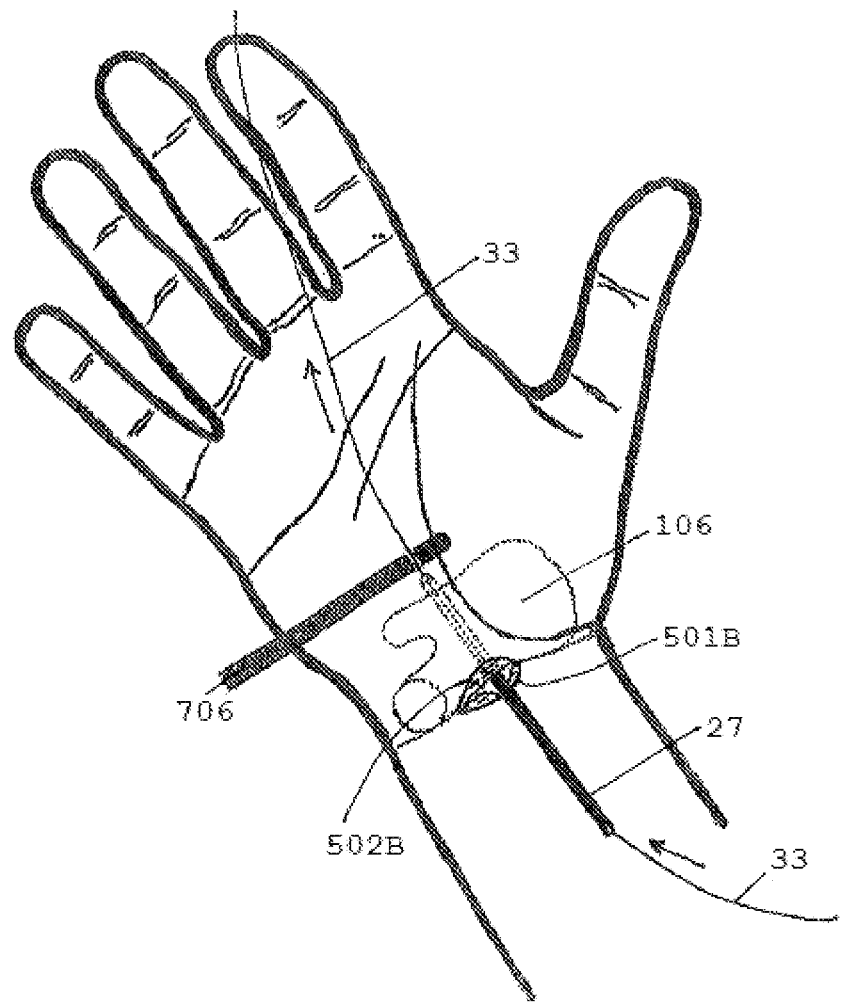
FIG. 5A is a schematic view of a human palm and wrist showing:
1) a flexible metal guide needle being introduced underneath the deep surface of the transverse carpal ligament (TCL) through the lumen of the curved tip cannulated guide rod which is part of the invention described herein during the procedure which is the subject hereof and, 2) The palm of the hand distal to the referenced line of Kaplan being pressured down with a blunt spatula to facilitate the extrusion of the tip of the flexible needle, in which numbers represent the same as indicated under FIG. 5B.
Figure 5B:
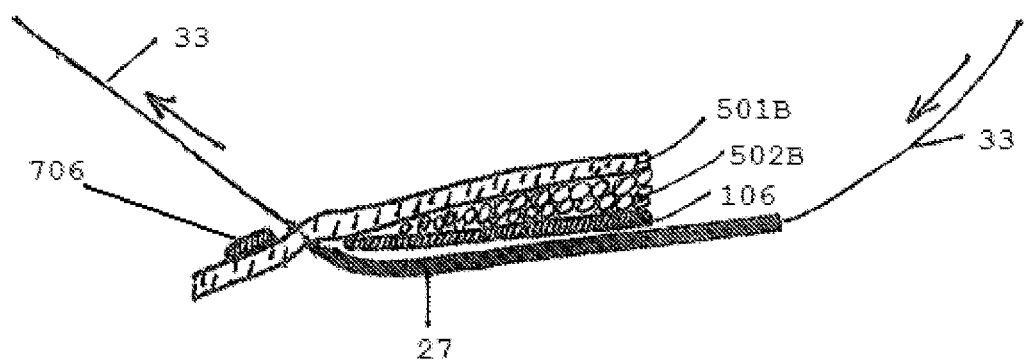
FIG. 5B is a larger scale, sagital view, of a portion of FIG. 5A showing the same procedure illustrated in the previous figure, in which numbers represent the following:
- 27—Shaft of the curved tip cannulated guide rod;
- 33—Flexible metal guide needle;
- 106—Transverse carpal ligament (TCL);
- 305—Surgical Incision;
- 405—Proximal edge of the transverse carpal ligament (TCL);
- 501B—Skin;
- 502B—Subcutaneous fat;
- 706—Spatula.

Once again, manual digital feeling must be used. A blunt spatula (706) is placed over the skin of the palm pressing down just distal to the felt tip of the curved tip cannulated guide rod (27) and, with the help of an assistant, a flexible metal guide needle (33) (CONMED/Linvatec: Doubled Armed Suture Needle, REF 8535), is passed along the lumen of the rod until its sharp tip is made to protrude through the skin of the palm as shown if FIGS. 5A and B. The surgeon must observe that the tip of the needle is, in fact, positioned in the "safe zone", in line with the ring finger and less than 10 mm distal to the marked cardinal line of Kaplan. If not, the surgeon must retrieve the needle, reposition the curved tip cannulated guide rod and try again.

Figure 6:
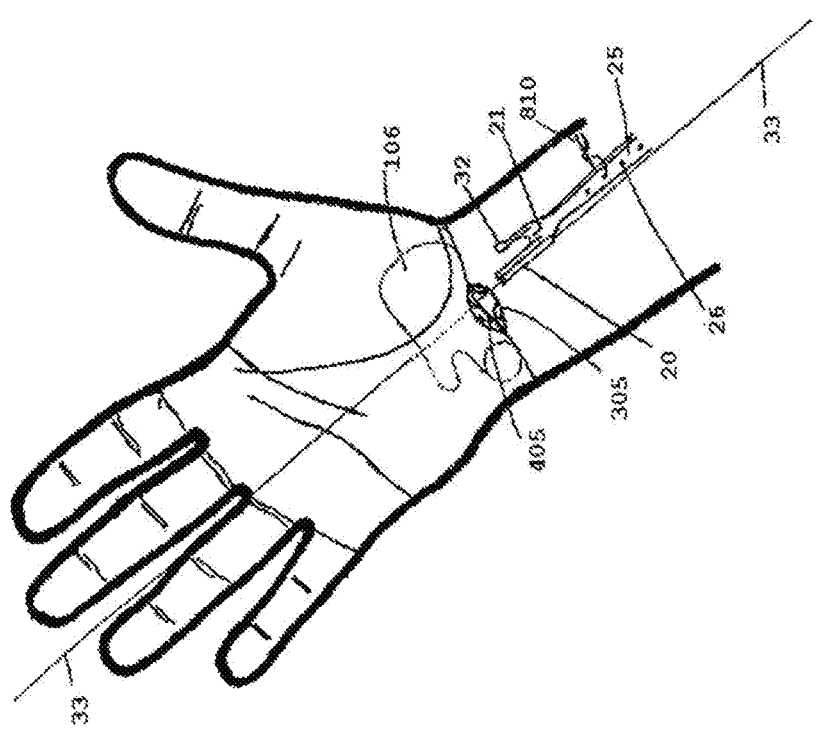
FIG. 6 is a schematic view of a human palm and wrist showing the cannulated finger-like prong of the distal end of the transverse carpal ligament fasciotome which is part of the invention described herein introduced along the flexible metal guide needle placed underneath the transverse carpal ligament (TCL), during the procedure which is the subject hereof, in which numbers represent the following:
- 20—Canulated finger-like prong;
- 21—Blade (knife cutting edge);
- 25—Fasciotome;
- 26—Fenestrations in the fasciotome shaft;
- 32—Metal sphere;
- 33—Flexible metal guide needle;
- 106—Transverse carpal ligament (TCL);
- 305—Surgical Incision;
- 405—Proximal edge of the transverse carpal ligament (TCL);
- 810—Wire.
Figure 7:
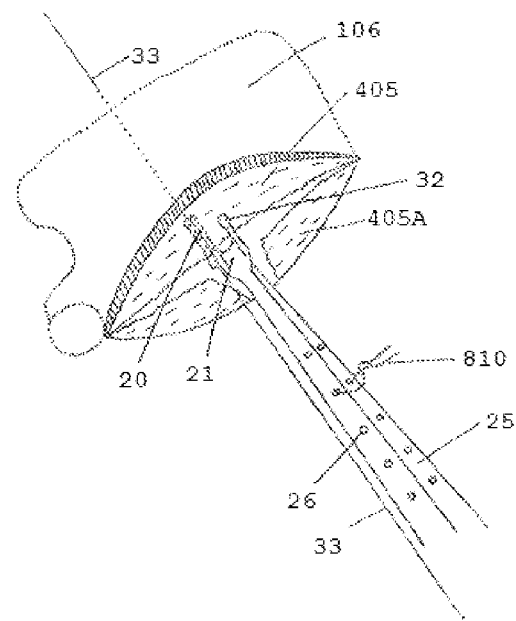
FIG. 7 is a schematic view of a human palm and wrist with the transverse carpal ligament (TCL) fasciotome which is part of the invention described herein being engaged in the proximal edge of the transverse carpal ligament (TCL), straddling the ligament, under guidance of the flexible metal guide needle kept under tension with the aid of two strong needle holders (not shown), during the procedure which is the subject hereof, in which numbers represent in which numbers represent the following:
- 20—Cannulated finger-like prong;
- 21—Blade (knife cutting edge);
- 25—Fasciotome;
- 26—Fenestrations in the fasciotome shaft;
- 32—Metal sphere;
- 33—Flexible metal guide needle;
- 106—Transverse carpal ligament (TCL)

Once the surgeon is satisfied with the position of the needle, the said guide rod (27) is retrieved and, the straight transverse carpal ligament fasciotome (25) comes into play as shown in FIG. 6. The surgeon may begin by placing the fasciotome flat on top of the palm of the hand, so that the cutting edge of the blade (21) is in close proximity to the flexible metal guide wire (33) at the exact spot where it protrudes through the skin (not shown). The fenestration in the shaft of the fasciotome that is closest to the distal edge of the surgical incision (305) will also provide the surgeon with an estimate of the length of fasciotome that must introduced across the TCL (106) to achieve a complete cut. Across this fenestration, the surgeon can introduce a metal device, like a piece of wire (810) or simply a thin, e.g. 23G, hypodermic needle loosely folded around the fasciotome shaft, as shown in FIGS. 6 and 7. This will serve as a guide for the surgeon not to introduce the fasciotome into the palm of the hand beyond the marked spot, as shown if FIGS. 8A, B and C, therefore, preventing iatrogenic lesions to any hand structures distal to the distal edge of the TCL (106), namely the superficial arterial palmar arch (not shown). The following step is to feed the flexible metal guide needle through the lumen of the cannulated finger-like prong (20), as shown in FIG. 6. Next, the prongs are orientated so that the blade edge of the fasciotome straddles the proximal edge of the ligament as shown in FIG. 7. The upper prong with its tip sphere (32) must be accurately placed, under direct vision, on top of the proximal edge of the ligament; the lower part of the blade end must also be accurately placed, under direct vision, below the under surface of the ligament. This is a critical step in the operative technique.

Once the surgeon is absolutely sure of the position of the fasciotome blade in relation to the edge of the TCL, the flexible metal guide needle (33) must be put under tension, with the help of an assistant pulling it in opposite directions with, e.g., heavy needle holders (not shown). At this point, it is also helpful if he slightly lifts the needle in order to push it against the under surface of the ligament. By this manoeuvre the hand is brought into neutral or slightly extended position. The fasciotome (25), under the guidance of said needle (33) is then pushed all the way distally across the ligament, cutting it, until its distal tip abuts against the deep surface of the palmar skin as shown in FIGS. 8A, B and C. Also, at the end of this manoeuvre, the wire marker must be at the level of the proximal edge of the TCL, as shown in FIG. 8-A.

Optionally, prior to the introduction of the knife (25), the slotted cannulated tip guide cannula (40) can be advanced first along the flexible metal guide needle (33) into the palm of the hand, until its end abuts against the under surface of the skin, at the point where the needle crosses the skin of the palm, from deep to the surface, as shown is FIGS. 9-A and B. The rational for this alternative is to further increase safety, the cannula protecting the tissues underneath the TCL (106). After the slotted cannula (40) is in place, the fasciotome (25), under the guidance of the flexible metal guide needle (33) fed through its inferior cannulated finger-like prong (20), as previously described, is slid over the longitudinal slot of the cannula, as shown in FIG. 9-C, all the way across the TCL as shown in FIG. 9-D.

After the TCL (106) is cut, we retrieve the instruments and routinely check in order to ascertain and document that the ligament was completely divided. For this purpose, we lift up the palmar skin and its underlying fat pad with an elevator (not shown) and insert into the wound a 0° degree angle scope (not shown). If there is any doubt about some remaining fibbers at the distal part of the ligament we then insert (not shown), under direct vision of the scope, a Stephenson type of knife and cut through those most distal fibbers. Otherwise, only a picture is taken for documentation purposes. The palmar skin is closed with two or three absorbable stitches (not shown) and the hand is dressed appropriately.

The invention claimed is:

1. A surgical instrument for precision cutting comprising:
   a blade having an edge;
   a first solid prong attached to the blade and projecting a first distance away from the edge of the blade;
   a tubular prong attached to the first solid prong, the tubular prong comprising a hollow cylinder, the tubular cylinder projecting a second distance away from the edge of the blade, the second distance being greater than the first distance, the tubular prong being adapted to allow passage of a flexible guide wire needle into and through the hollow cylinder; and
   a second solid prong attached to the blade and projecting away from the edge of the blade
   wherein the blade has a proximal end and a distal end and the tubular prong has a proximal end and a distal end,
   wherein the proximal end of the blade extends to a position more proximal than the proximal end of the tubular prong.

2. The surgical instrument according to claim 1, further comprising a cannulated guide rod adapted to receive, allow passage of, and guide a flexible guide wire needle that is adapted to guide the blade during a cutting operation.

3. The surgical instrument according to claim 2, wherein the cannulated guide rod comprises a cannulated cylindrical rod with two open ends, wherein one of the two open ends is curved.

4. The surgical instrument according to claim 2, wherein:
   the cannulated guide rod comprises a border having a curved tip, the curved tip having a concave side, the curved tip further having a protrusion; and
   shaft comprises, on the concave side, an engraved metric scale.

5. The surgical instrument according to claim 2, wherein the a metal sphere is connected to a tip of the first solid prong.

6. The set of surgical instrument according to claim 1, wherein the second solid prong projects a third distance away from the edge of the blade, the third distance being smaller than the first distance, and wherein a metal sphere is connected to a tip of the second solid prong.

7. The surgical instrument according to claim 1, wherein the first solid prong is connected to one of the centre, the right side, or the left side of a distal inferior end of the surgical instrument.

8. The set of surgical instrument according to claim 1, further comprising:
   two parallel cannulated prongs and a central solid prong.

9. The set of surgical instrument according to claim 1, further comprising:
   a shaft joined to the blade; and
   guiding holes disposed in the shaft, wherein adjacent guiding holes are separated from each other situated at an equal by a uniform distance.

10. The surgical instrument according to claim 9, further comprising:
    a handle attached to the shaft, the handle having a longitudinal axis and a concavity facing away from the shaft, wherein the handle does not protrude below an inferior surface of the shaft.

11. The surgical instrument according to claim 1, further comprising:
    a sphere connected to a tip of the first solid prong.

12. The surgical instrument according to claim 1 further comprising:
  a shaft attached to the blade, the shaft being bent at a 90° angle in a distal portion;
  with a superior and inferior finger-like blunt prongs, having a metal sphere attached to a tip of the first solid prong, the metal sphere being at least 2 mm in diameter.

13. The surgical instrument according to claim 12, further comprising:
  a guide cannula adapted to receive, allow passage of, and guide the flexible guide wire needle, the flexible guide wire needle being adapted to guide the blade during a cutting operation.

14. The surgical instrument according to claim 1, further comprising:
  a guide cannula adapted to receive, allow passage of, and guide a flexible guide wire needle adapted to guide the blade during a cutting operation.

15. The surgical instrument according to claim 14, wherein the guide cannula is a straight, elongated cannula, having a closed end and an open end, and a longitudinal slot adapted to receive a flexible metal guide needle and guide the blade, wherein the open end of the guide cannula has at least two handles, and the closed end of the guide cannula is fenestrated, having a hole adapted to allow passage of the flexible metal guide needle.

16. The surgical instrument according to claim 15, wherein the guide cannula has one of a semi-circular restraining metal arch and an arch-brake over a rim formed along the longitudinal slot.

17. The surgical instrument according to claim 14, wherein the guide cannula has a longitudinal slot adapted to accommodate the flexible metal guide needle and has a plurality of end-side handles adapted to facilitate handling of the guide cannula.

* * * * *